(12) United States Patent
Imai

(10) Patent No.: US 11,540,799 B2
(45) Date of Patent: Jan. 3, 2023

(54) MEDICAL APPARATUS, AND PROGRAM

(71) Applicant: General Electric Company, Schenectady, NY (US)

(72) Inventor: Yasuhiro Imai, Tokyo (JP)

(73) Assignee: General Electric Company, Schenectady, NY (US)

( * ) Notice: Subject to any disclaimer, the term of this patent is extended or adjusted under 35 U.S.C. 154(b) by 65 days.

(21) Appl. No.: 17/120,724

(22) Filed: Dec. 14, 2020

(65) Prior Publication Data

US 2021/0186452 A1   Jun. 24, 2021

(30) Foreign Application Priority Data

Dec. 24, 2019 (JP) .............................. JP2019-232956

(51) Int. Cl.
*A61B 6/00* (2006.01)

(52) U.S. Cl.
CPC .............. *A61B 6/542* (2013.01); *A61B 6/468* (2013.01); *A61B 6/5211* (2013.01)

(58) Field of Classification Search
CPC ......... A61B 6/00; A61B 6/542; A61B 6/5211; A61B 6/468; A61B 6/032; A61B 6/465; A61B 6/46; A61B 6/488; A61B 6/545; A61B 6/54
See application file for complete search history.

(56) References Cited

U.S. PATENT DOCUMENTS 9,044,197 B2 *   6/2015   Richard ................. A61B 6/544

FOREIGN PATENT DOCUMENTS

JP           2015-43972 A        3/2015

* cited by examiner

*Primary Examiner* — Jurie Yun

(57) ABSTRACT

To provide a technique with which dose indices can be managed for body parts in a range to be imaged on a body part-by-body part basis, an X-ray CT apparatus comprises: image producing unit (51) for producing a scout image (10) of a patient; defining unit (52) for defining a range (11) to be imaged in the scout image (10); segmenting unit (53) for segmenting the range (11) to be imaged into two body parts; identifying unit (54) for identifying which one of body parts (12) included in a human body each of the two body parts corresponds to; and calculating unit (55) for calculating a dose index for each of the two body parts.

12 Claims, 15 Drawing Sheets

FIG. 13

Dose Report

Patient Name:
Accession Number:
Patient ID:1
Exam Description:feet

| Series | Type | Scan Range (mm) | CTDIvol (mGy) | DLP (mGy-cm) |
|---|---|---|---|---|
| 1 | Scout | — | — | — |
| 200 | Axial | xx.xxx-xx.xxx | x.xx | x.xx |
| 2 | Axial | xx.xxx-xxx.xxx | xx.xx | xx.xx |
| 3 | SmartView | xxx.xxx-xxx.xxx | x.xx | x.xx |
| 3 | SmartView | xxx.xxx-xxx.xxx | x.xx | x.xx |

SmartView Accumulated DLP: x.xx
Total Exam DLP: xx.xx
SmartView Accumulated Exposure time xx:xx:xx.x

MAIN SCAN

FIG. 14

Dose Report

Patient Name:
Accession Number:
Patient ID:1
Exam Description:feet

| Series | Type | Scan Range (mm) | CTDIvol (mGy) | DLP (mGy-cm) |
|---|---|---|---|---|
| 1 | Scout | — | — | — |
| 200 | Axial | xx.xxx-xx.xxx | x.xx | x.xx |
|  | CH | xx.xxx-xx.xxx | x.xx | x.xx |
|  | AB | xx.xxx-xxx.xxx | xx.xx | xx.xx |
| 2 | Axial | xxx.xxx-xxx.xxx | x.xx | x.xx |
| 3 | SmartView | xxx.xxx-xxx.xxx | x.xx | x.xx |
| 3 | SmartView |  |  |  |

(Axial, CH, AB, Axial rows enclosed by dashed box labeled MAIN SCAN)

SmartView Accumulated DLP: x.xx
Total Exam DLP: xx.xx
SmartView Accumulated Exposure time xx:xx:xx.x

MEDICAL APPARATUS, AND PROGRAM

FIELD

The present invention relates to a medical apparatus for acquiring an image of a patient using radiation, and a program applied to the medical apparatus.

BACKGROUND

X-ray CT apparatuses have been known as apparatuses for non-invasively imaging a patient. The X-ray CT apparatuses are installed in various medical institutions because of its ability to acquire images of a patient in a short period of time.

Once a scan has been performed on a patient by the X-ray CT apparatus and the imaging of the patient has been completed, a dose report including information on the patient's exposure (dose index) is created. The X-ray CT apparatus sends the dose report to a server. The server receives the dose report, and manages it.

A radiologic technologist can download the dose report from the server to an operation console of the X-ray CT apparatus, as needed, even after imaging of the patient. The radiologic technologist can thus confirm the patient's exposure in the past imaging from the dose report. Moreover, in the case that a patient underwent X-ray CT imaging more than once in the past, the radiologic technologist can also confirm the patient's exposure in X-ray CT imaging performed in the past on a session-by-session basis from the dose report, and thus, a temporal tracking of the patient's exposure can be recognized. Furthermore, by confirming the patient's exposure, a rough estimate of the exposure allowed for the patient in current imaging can be known.

Therefore, management of a dose report created in imaging of a patient on a session-by-session basis is important in performing imaging on the patient with appropriate imaging conditions.

Patent Document 1: Gazette of Japanese Patent Application KOKAI No. 2015-43972

In performing imaging on a patient, a radiologic technologist specifies a range to be imaged in the patient prior to performing a scan. The range to be imaged generally and frequently includes more than one body part. For example, the radiologic technologist may sometimes specify a range to be imaged including a head and a neck, and at other times that including a chest and an abdomen. In such cases, in the dose report is recorded a dose index regarding a plurality of body parts included in the range to be imaged as if they were one body part. However, the effect of exposure on the range to be imaged is actually not the same among body parts included in the range to be imaged, and tends to be different from body part to body part included in the range to be imaged. Therefore, it is desirable to manage a dose index for the whole range to be imaged, and in addition, dose indices for body parts included in the range to be imaged on a body part-by-body part basis. However, in the case that a plurality of body parts are included in a range to be imaged, there is a problem that although a conventional dose report enables one to know a dose index for the whole range to be imaged, it does not allow one to know dose indices for body parts included in the range to be imaged on a body part-by-body part basis.

Accordingly, it is desired to provide a technique with which dose indices can be managed for body parts in a range to be imaged on a body part-by-body part basis.

SUMMARY

This summary introduces concepts that are described in more detail in the detailed description. It should not be used to identify essential features of the claimed subject matter, nor to limit the scope of the claimed subject matter.

The present invention, in its first aspect, is a medical apparatus comprising:

image producing means for producing an image of at least part of a patient;

defining means for defining a range to be imaged in said image;

segmenting means for segmenting said range to be imaged into a plurality of body parts;

identifying means for identifying which one of body parts included in a human body each of said plurality of body parts corresponds to; and calculating means for calculating a dose index for each of said plurality of body parts.

The present invention, in its second aspect, is a program for causing a processor to execute:

image producing processing of producing an image of at least part of a patient;

defining processing of defining a range to be imaged in said image;

segmenting processing of segmenting said range to be imaged into a plurality of body parts;

identifying processing of identifying which one of body parts included in a human body each of said plurality of body parts corresponds to; and calculating processing of calculating a dose index for each of said plurality of body parts.

The present invention, in its third aspect, is a non-transitory, computer-readable recording medium provided in a medical apparatus for acquiring an image of a patient, in which medium are stored one or more processor-executable instructions causing, when executed by said processor, execution of the acts comprising:

(a) producing an image of at least part of a patient;

(b) defining a range to be imaged in said image;

(c) segmenting said range to be imaged into a plurality of body parts;

(d) identifying which one of body parts included in a human body each of said plurality of body parts corresponds to; and (e) calculating a dose index for each of said plurality of body parts.

Since a range to be imaged is segmented into a plurality of body parts, the range to be imaged may be divided into a plurality of body parts for each of which a dose index should be managed. Dose indices are then calculated for the body parts in the segmented range to be imaged on a body part-by-body part basis. Therefore, even when a range to be imaged includes a plurality of body parts for each of which a dose index should be managed, dose indices can be determined on a body part-by-body part basis.

BRIEF DESCRIPTION OF THE DRAWINGS

FIG. 13 is a diagram showing an example of a displayed dose report.

FIG. 14 is a diagram showing an example of a dose report 13 representing numeric values of fields for the chest and those for the abdomen.

DETAILED DESCRIPTION

Embodiments of the present disclosure will now be described, by way of example, with reference to the Figures, and the present invention is not limited thereto.

Figure 1:
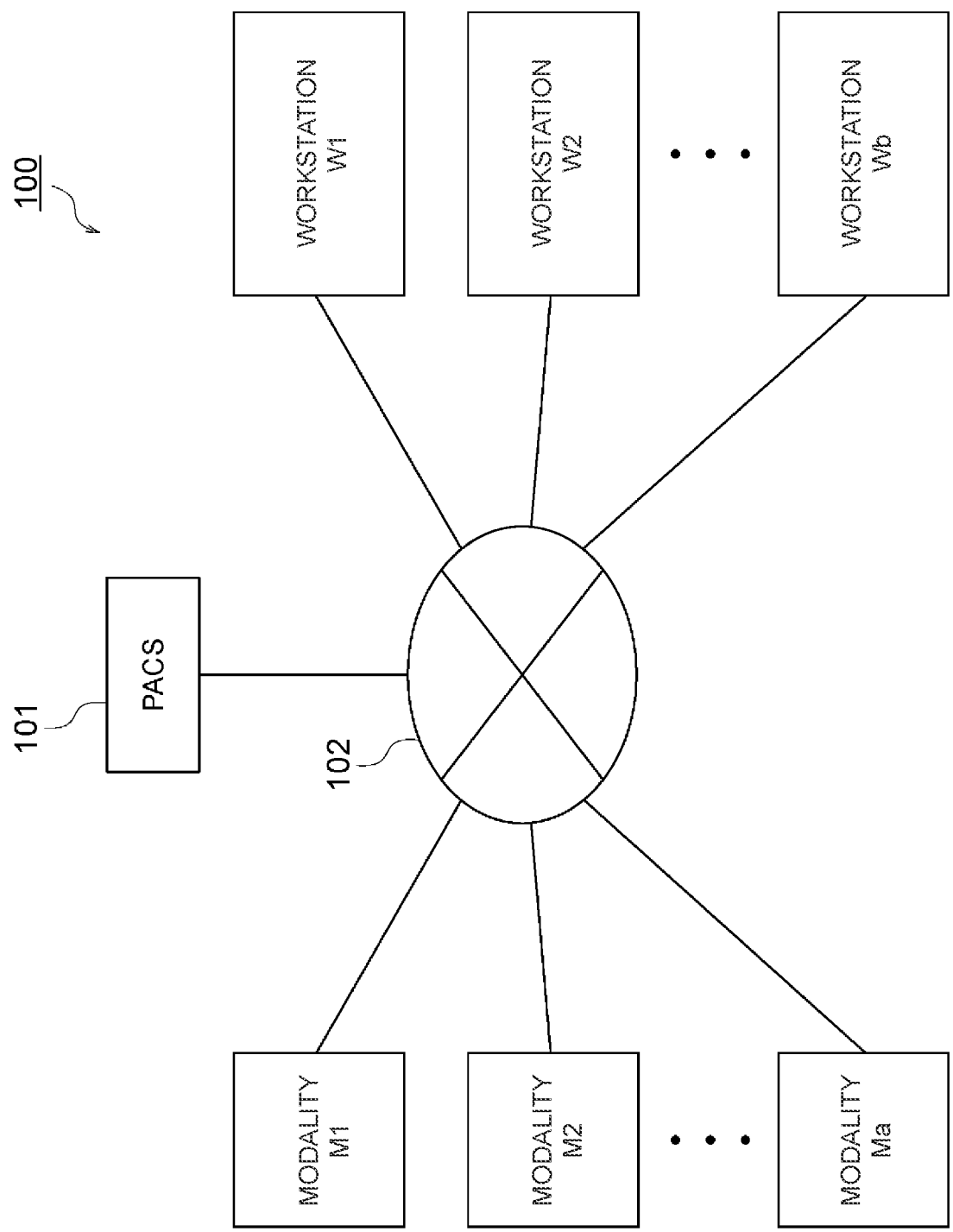
FIG. 1 is a diagram showing a medical information management system 100 comprising a medical apparatus in one embodiment of the present invention.

FIG. 1 is a diagram showing a medical information management system 100 comprising a medical apparatus in one embodiment of the present invention.

The system 100 comprises a plurality of modalities M1 to Ma. The plurality of modalities M1 to Ma include radiation-based ones performing diagnosis and/or treatment on a patient, such as an X-ray CT apparatus and a PET-CT apparatus, and non-radiation-based ones performing diagnosis, etc. on a patient, such as an MRI apparatus.

The system 100 also has a PACS (Picture Archiving and Communication Systems) 101. The PACS 101 receives data of images, etc. acquired in the modalities via a communication network 102, and archives the received data. The PACS 101 also transfers the archived data via the communication network 102, as needed.

Moreover, the system 100 has a plurality of workstations W1 to Wb. These workstations W1 to Wb are, for example, those used in a hospital information system (HIS), a radiology information system (RIS), a clinical information system (CIS), a cardiovascular information system (CVIS), a library information system (LIS), an electronic medical record (EMR) system, and/or any other image and information management system, and those used in image inspection works by radiologists.

The system 100 is thus constructed as above. Next, an example of a configuration of an X-ray CT apparatus, which is an example of the modalities, will be described.

Figure 2:
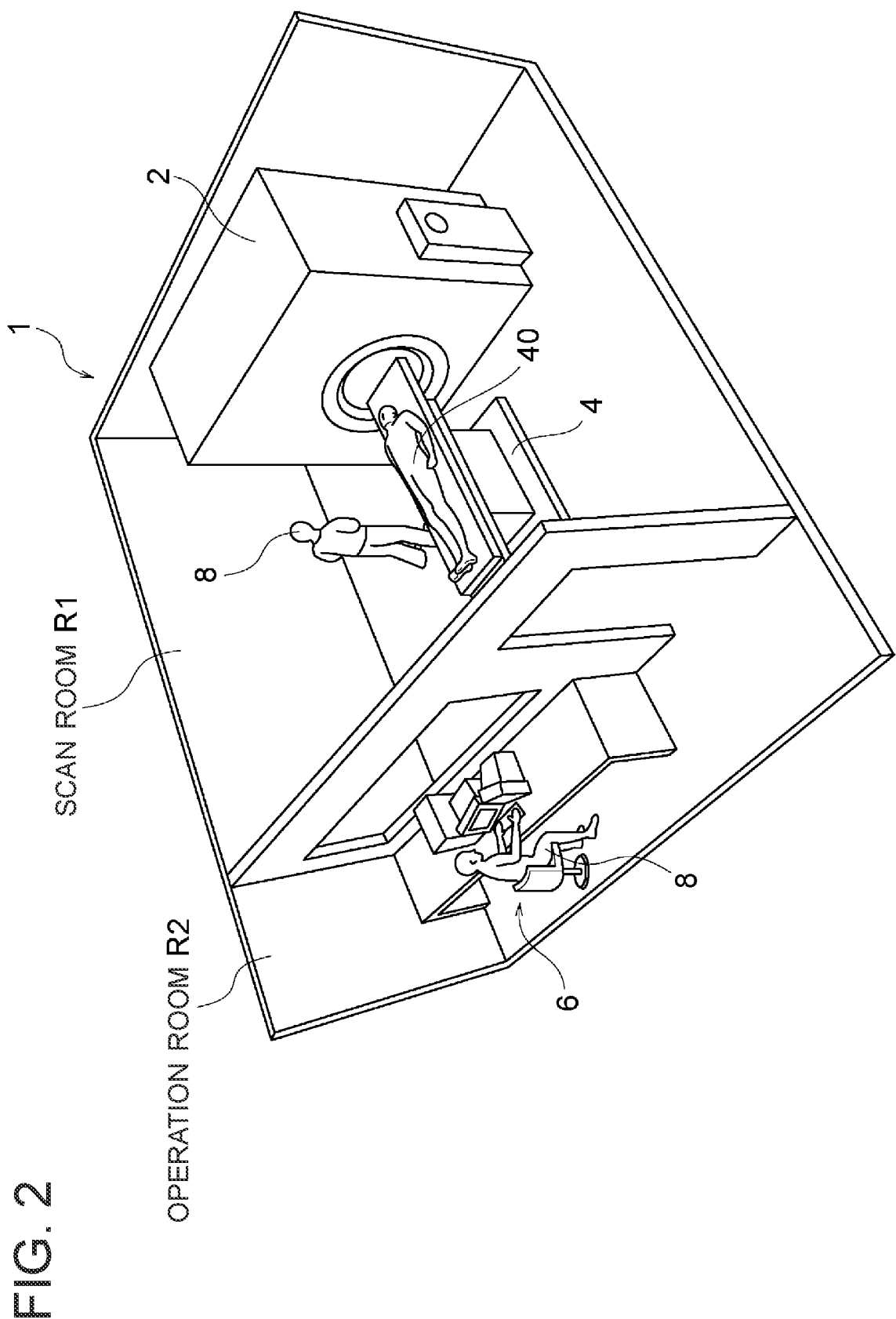
FIG. 2 is a diagram schematically showing an external view of an X-ray CT apparatus.

FIG. 2 schematically shows an external view of an X-ray CT apparatus.

As shown in FIG. 2, an X-ray CT apparatus 1 comprises a gantry 2, a table 4, and an operation console 6.

The gantry 2 and table 4 are installed in a scan room R1, while the operation console 6 is installed in an operation room R2.

Figure 3:
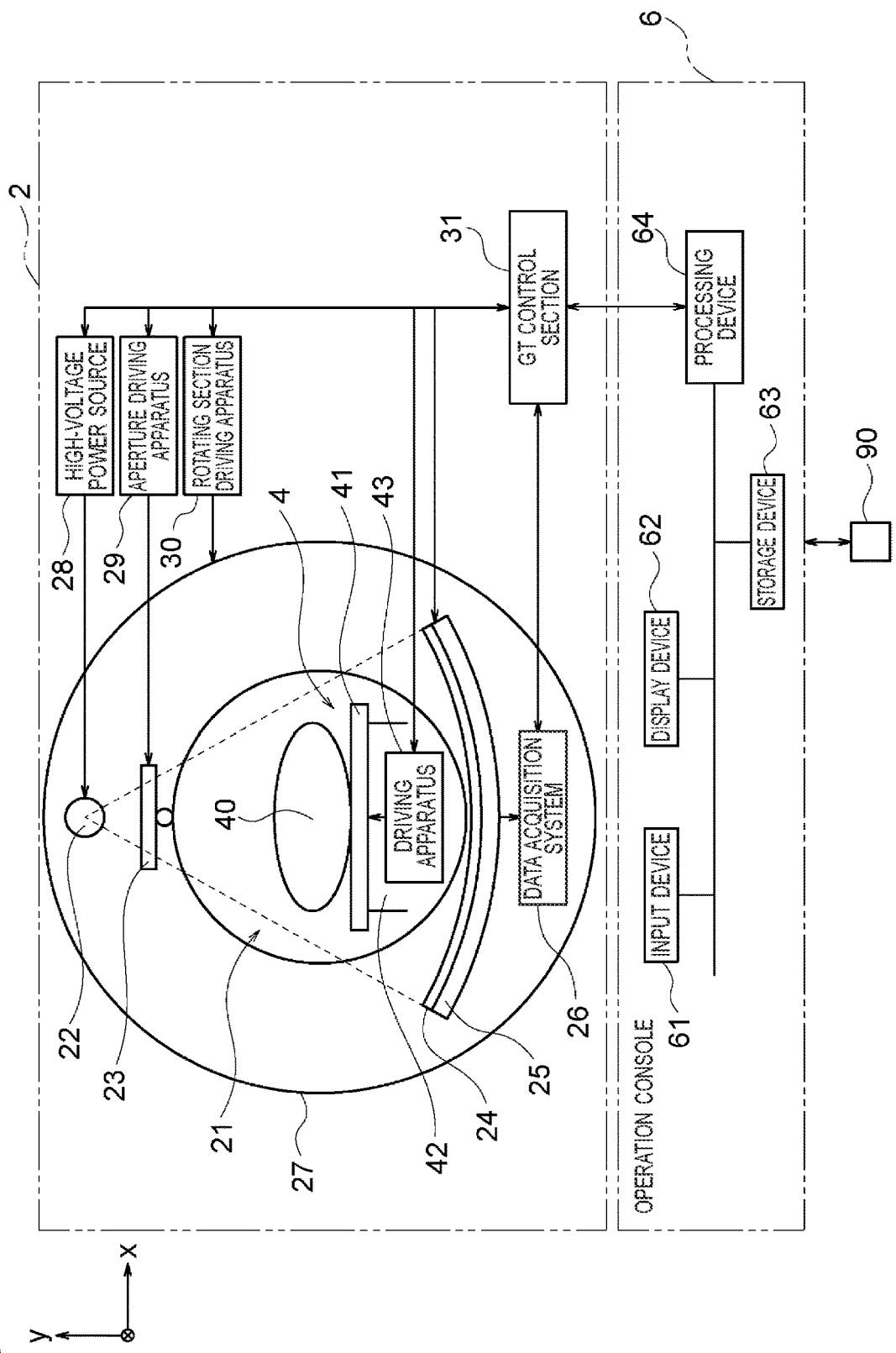
FIG. 3 is a block diagram of the X-ray CT apparatus.

FIG. 3 is a block diagram of the X-ray CT apparatus.

The gantry 2 has a bore 21 for forming space through which a patient 40 can be moved.

The gantry 2 also has an X-ray tube 22, an aperture 23, a collimator 24, an X-ray detector 25, a data acquisition system 26, a rotating section 27, a high-voltage power source 28, an aperture driving apparatus 29, a rotating section driving apparatus 30, a GT (Gantry Table) control section 31, etc.

The X-ray tube 22, aperture 23, collimator 24, X-ray detector 25, and data acquisition system 26 are mounted on the rotating section 27.

The X-ray tube 22 and X-ray detector 25 are disposed facing each other sandwiching the bore 21 of the gantry 2.

The aperture 23 is disposed between the X-ray tube 22 and bore 21. The aperture 23 shapes X-rays emitted from an X-ray focus of the X-ray tube 22 toward the X-ray detector 25 into a fan beam or a cone beam.

The X-ray detector 25 detects X-rays passing through the patient 40.

The collimator 24 is disposed on a side of X-ray entrance with respect to the X-ray detector 25, for removing scattered X-rays.

The high-voltage power source 28 supplies high voltage and electric current to the X-ray tube 22.

The aperture driving apparatus 29 drives the aperture 23 to modify the shape of its opening.

The rotating section driving apparatus 30 rotationally drives the rotating section 27.

The GT control section 31 controls several apparatuses and sections in the gantry 2, a driving apparatus 43, etc.

The table 4 has a cradle 41, a cradle support base 42, and the driving apparatus 43. The cradle 41 is for supporting the patient 40 undergoing imaging. The cradle support base 42 is for supporting the cradle 41 movably in y- and z-directions. The driving apparatus 43 is for driving the cradle 41 and cradle support base 42. Here, a direction of a body axis of the patient 40 is defined as the z-direction, a vertical direction as the y-direction, and a horizontal direction perpendicular to the z- and y-directions as an x-direction.

The operation console 6 has an input device 61, a display device 62, a storage device 63, a processing device 64, etc.

The input device 61 comprises a keyboard and a pointing device, etc. for accepting an input of a command and/or information from a radiologic technologist, and performing several kinds of operations. The display device 62 is for displaying visual information including images, etc., and is, for example, an LCD (Liquid Crystal Display), an organic EL (Electro-Luminescence) display, or the like.

In the storage device 63 are stored programs for the processor to execute several kinds of processing. The storage device 63 also stores therein several kinds of data, several kinds of files, etc. The storage device 63 has an HDD (Hard Disk Drive), DRAM (Dynamic Random Access Memory), ROM (Read Only Memory), etc. The storage device 63 may include a portable storage medium 90, such as a CD (Compact Disk), a DVD (Digital Versatile Disk), or the like.

The processing device 64 performs image reconstruction processing based on data for the patient 40 acquired with the gantry 2, and performs several other kinds of computations. The processing device 64 has one or more processors, which execute several kinds of processing corresponding to the programs stored in the storage device 63.

The X-ray CT apparatus 1 is thus configured as above.

One of characteristic functions of the X-ray CT apparatus 1 in the present embodiment is to create a dose report for a patient. Accordingly, some of the functions the X-ray CT apparatus 1 has that is particularly related to creation of a dose report for a patient will be described hereinbelow.

Figure 4:
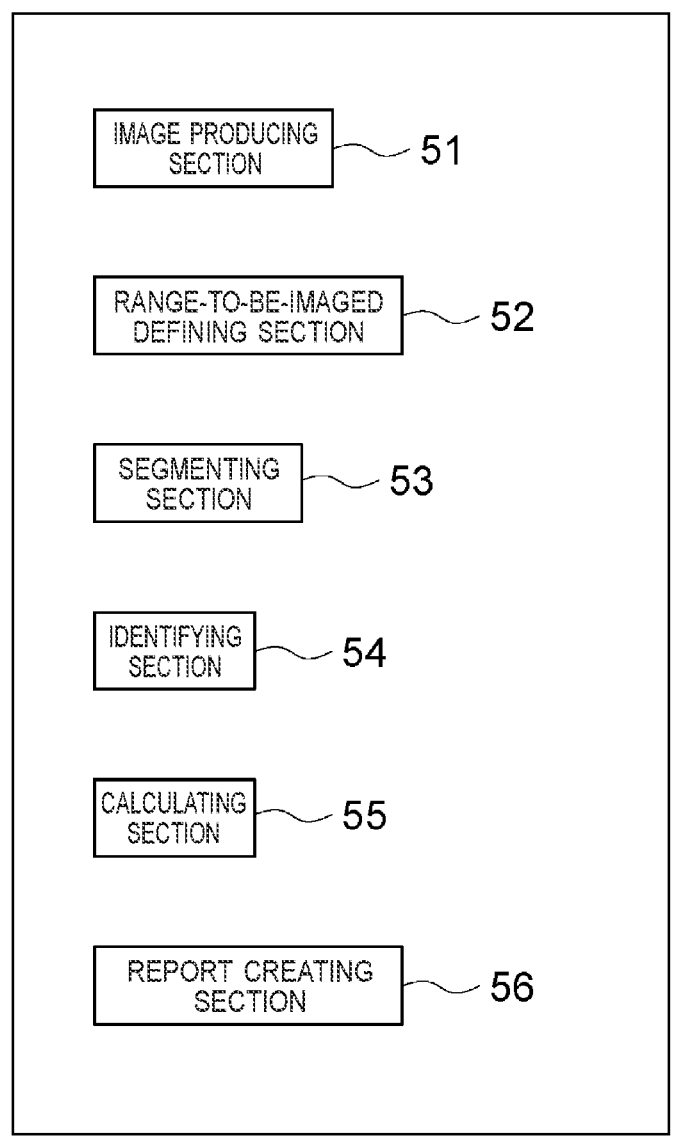
FIG. 4 is a functional block diagram of the X-ray CT apparatus.

FIG. 4 is a functional block diagram of the X-ray CT apparatus.

The X-ray CT apparatus is configured to execute the following functions 51 to 56:

An image producing section 51 executes processing of producing a CT image of a patient based on data acquired by a scan.

A range-to-be-imaged defining section 52 executes processing of defining a range to be imaged in the patient.

A segmenting section 53 executes processing for segmenting the range to be imaged defined by the range-to-be-imaged defining section 52 into a plurality of body parts. The segmenting section 53 executes, for example, processing of fixing a line for segmenting the range to be imaged into the plurality of body parts. The line will be discussed later.

An identifying section 54 identifies which one of body parts included in a human body each body part included in the range to be imaged corresponds to. The identifying section 54 can identify a body part by, for example, selecting a body part included in the range to be imaged from within a list representing the body parts included in the human body. The list will be discussed later.

A calculating section 55 calculates numeric values of fields (for example, scan ranges and dose indices) required in a dose report for the body parts included in the range to be imaged on a body part-by-body part basis.

A report creating section 56 creates a dose report based on the numeric values calculated by the calculating section 55.

In the storage device 63 are stored programs representing the processing of the functional blocks described above. The storage device 63 may be a non-transitory, computer-readable recording medium in which one or more processor-executable instructions are stored. The one or more instructions cause, when executed by the processor, execution of the acts comprising (a)-(f) below:

(a) producing an image of at least part of a patient (the image producing section 51);

(b) defining a range to be imaged in the image (the range-to-be-imaged defining section 52);

(c) segmenting the range to be imaged into a plurality of body parts (the segmenting section 53);

(d) identifying which one of body parts included in a human body each of the plurality of body parts corresponds to (the identifying section 54); and (e) calculating a dose index for each of the plurality of body parts (the calculating section 55); and (f) creating a dose report including the calculated dose indices (the report creating section 56).

Note that in place of the processor in the processing device 64, a processor in any other apparatus (for example, the display device) in the operation console 6 may execute the functional blocks described above. Moreover, it is possible to cause a processor included in the gantry 2 or table 4 to execute all or part of the processing of the functional blocks described above.

The X-ray CT apparatus is configured to execute the functions described above.

The medical information management system 100 shown in FIG. 1 is capable of managing dose indices for a patient acquired by each modality as a dose index for the whole range to be imaged, and in addition, as dose indices for the body parts in the range to be imaged on a body part-by-body part basis. Now a method by which the system 100 manages the dose indices will be described hereinbelow. While an example of managing dose indices for a patient will be described below taking an X-ray CT apparatus as a modality, the present invention may be applied to a case in which any radiation-based modality other than the X-ray CT apparatus (for example, a general X-ray imaging apparatus for imaging a chest or the like, a mammography imaging apparatus for imaging a breast, an angiographic imaging apparatus for contrast-imaging blood vessels, a PET-CT apparatus, or a SPECT-CT apparatus) is used.

Figure 5:
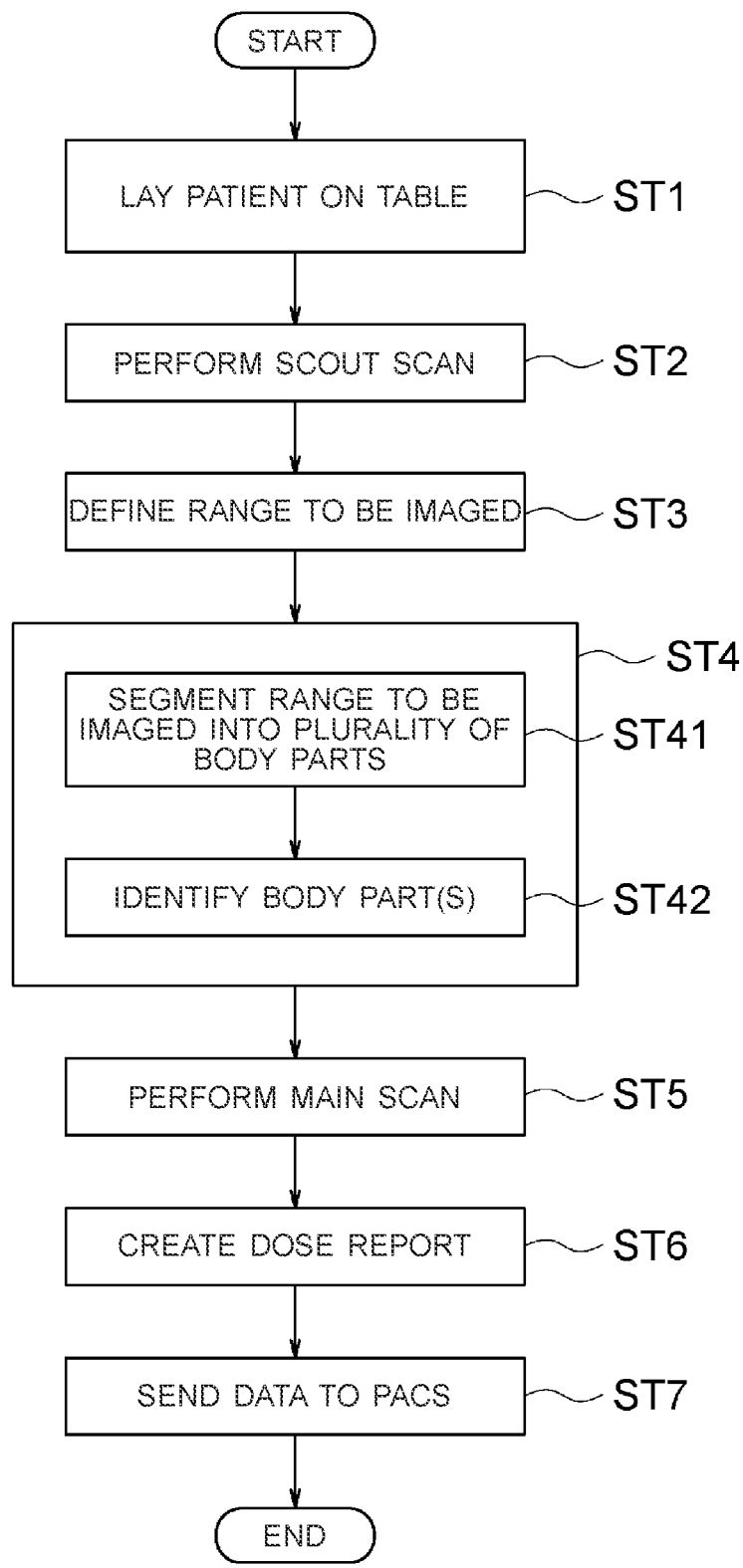
FIG. 5 is a chart showing the flow for managing dose indices for a patient.

FIG. 5 is a chart showing the flow for managing dose indices for a patient.

At Step ST1, the radiologic technologist 8 calls the patient 40 into the scan room R1, and lays the patient 40 on the table 4. The radiologic technologist 8 also sets imaging conditions (for example, a tube voltage, a tube current, an exposure time) for the patient 40.

At Step ST2, a scout scan is executed following the imaging conditions set in the X-ray CT apparatus. Data acquired by the scout scan is transmitted to the processing device 64 (see FIG. 3) in the operation console 6 from the gantry 2. The processor in the processing device 64 performs processing of image reconstruction based on the data acquired by the scout scan to produce a scout image. The processor in the processing device 64 executes the processing of producing the scout image by the function of the image producing section 51 (see FIG. 4).

Figure 6:
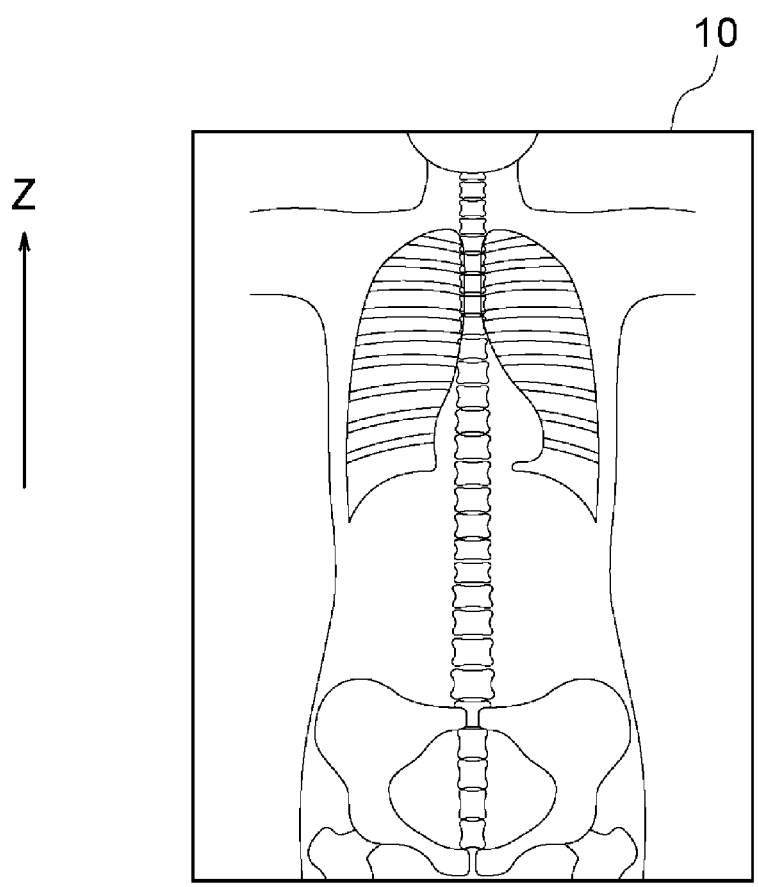
FIG. 6 is a diagram showing an example of a scout image.

FIG. 6 is a diagram showing an example of the scout image.

The scout scan can generally provide scout images in axial, sagittal, and coronal cross sections. FIG. 6 shows a scout image 10 in the coronal cross section as an example of the scout images. The scout image 10 is stored in the storage device 63 (see FIG. 3). After performing the scout scan, the flow goes to Step ST3.

Figure 7:
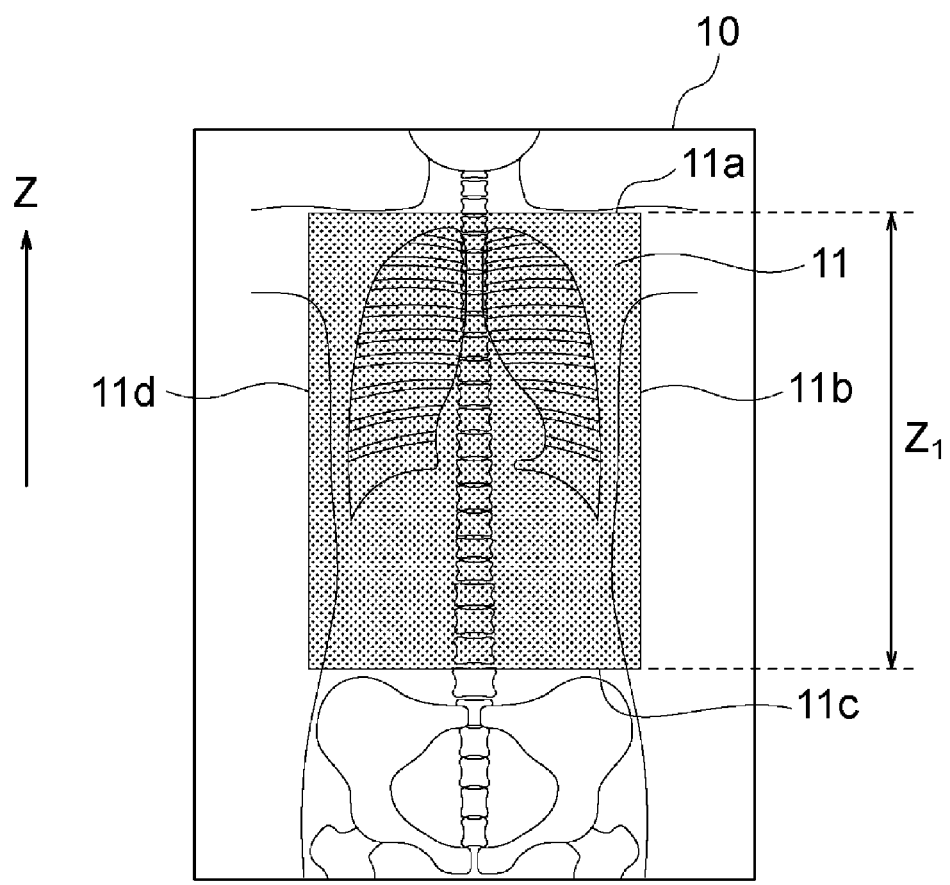
FIG. 7 is a diagram showing an example of a range 11 to be imaged in a main scan.

At Step ST3, the radiologic technologist 8 specifies a range to be imaged in a main scan (see FIG. 7).

FIG. 7 is a diagram showing an example of a range 11 to be imaged in the main scan.

The radiologic technologist 8 uses the input device 61 (see FIG. 3) to perform an operation for specifying a range to be imaged. The input device 61 inputs an operational signal corresponding to the operation by the radiologic technologist 8. In response to the operational signal input from the input device 61, the processor in the processing device 64 executes processing of defining the range 11 to be imaged in the scout image 10. The processor in the processing device 64 also instructs the display device 62 (see FIG. 3) to display the range 11 to be imaged. The display device 62 displays the range 11 to be imaged over the scout image 10. In FIG. 7, the range 11 to be imaged is shown as a range defined by four sides 11a-11d surrounding a region containing the chest and abdomen. The length of the range 11 to be imaged in the z-direction is set to z1. The processor in the processing device 64 executes the processing of defining the range to be imaged by the function of the range-to-be-imaged defining section 52 (see FIG. 4).

In the case that the radiologic technologist 8 desires to adjust the position of the range 11 to be imaged or the length thereof in the z-direction (body-axis direction), etc., (s)he uses the input device 61 to perform an operation for adjusting the range 11 to be imaged. The operation of adjusting the position of the range 11 to be imaged may involve, for example, an operation by the radiologic technologist 8 moving a cursor into the range 11 to be imaged and dragging a mouse. The operation of adjusting the length of the range 11 to be imaged in the z-direction may involve, for example, an operation by the radiologic technologist 8 moving the cursor onto the side 11c of the range 11 to be imaged and dragging the mouse.

When the radiologic technologist 8 has adjusted the range 11 to be imaged, the display device 62 displays the adjusted range 11 to be imaged over the scout image 10. The radiologic technologist 8 can thus confirm the adjusted range 11 to be imaged by looking at the display device 62. Range-to-be-imaged information (for example, the position of the range 11 to be imaged, the length thereof in the z-direction) for the range 11 to be imaged with respect to the scout image 10 is stored in the storage device 63 in association with the scout image 10.

After defining the range 11 to be imaged, the flow goes to Step ST4.

At Step ST4, the radiologic technologist 8 specifies a body part whose dose index (s)he desires to manage. Now Step ST4 will be described hereinbelow. Since Step ST4 includes Steps ST41 and ST42, they will be described in turn.

At Step ST41, the radiologic technologist 8 segments the range 11 to be imaged into a plurality of body parts whose dose indices (s)he desires to manage.

The radiologic technologist 8 uses the input device 61 to perform an operation for segmenting the range 11 to be imaged into a plurality of body parts whose dose indices (s)he desires to manage. Here is described a case in which the range 11 to be imaged is segmented into two body parts: a chest and an abdomen. Therefore, the radiologic technologist 8 uses the input device 61 to perform an operation for segmenting the range 11 to be imaged into the two body parts, the chest and abdomen. Now an example in which the range 11 to be imaged is segmented into the two body parts, the chest and abdomen, will be described hereinbelow.

Figure 8:
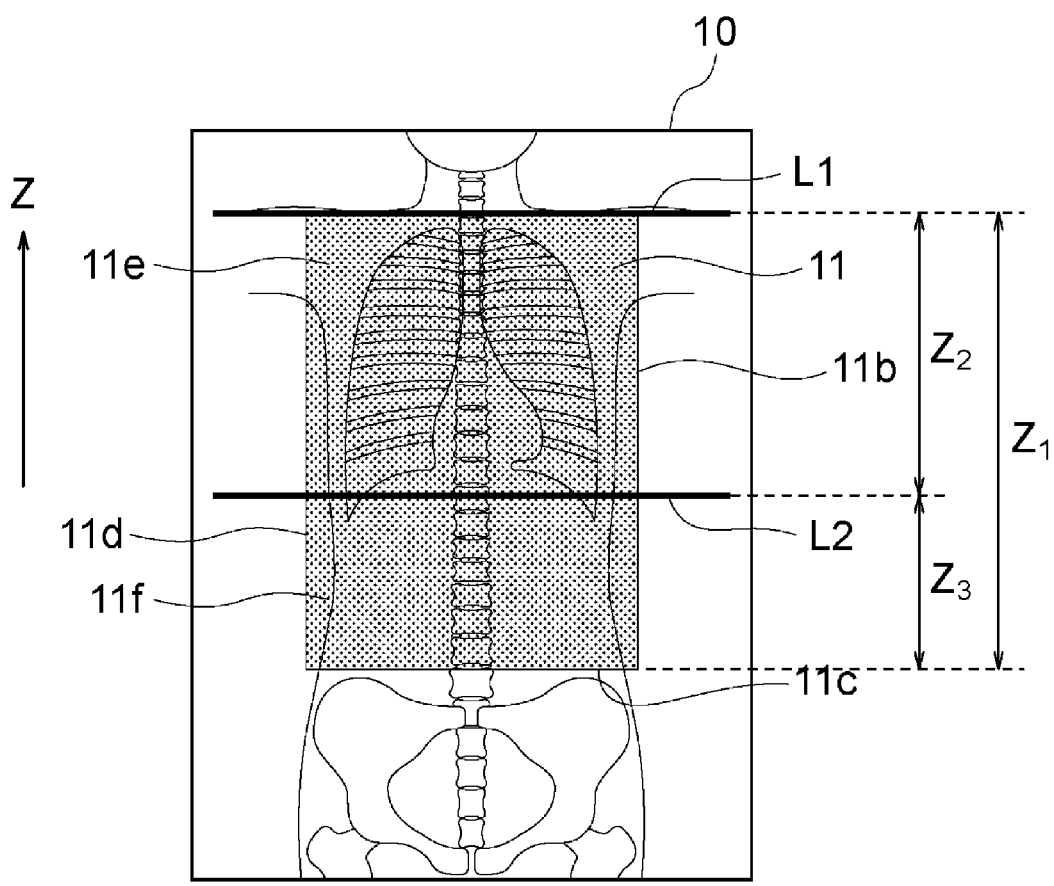
FIG. 8 is a diagram showing the range 11 to be imaged segmented into two body parts: a chest and an abdomen.

FIG. 8 is a diagram showing the range 11 to be imaged segmented into the two body parts, the chest and abdomen.

To segment the range 11 to be imaged into the two body parts, the chest and abdomen, the radiologic technologist 8 uses the input device 61 to perform an operation for drawing two lines L1 and L2 over the scout image 10. The operation for drawing the two lines L1 and L2 over the scout image 10 may involve, for example, an operation by the radiologic technologist 8 moving the cursor to a position at which (s)he desires to draw each of the lines L1 and L2, and performing a mouse-click.

In response to the operational signal input from the input device 61, the processor in the processing device 64 fixes the lines L1 and L2 for segmenting the range 11 to be imaged into the two body parts, the chest and abdomen. The processor in the processing device 64 also instructs the display device 62 to display the fixed lines L1 and L2. The display device 62 thus displays over the scout image 10 the lines L1 and L2 for segmenting the range 11 to be imaged into the two body parts, the chest and abdomen. The processor in the processing device 64 executes the processing of fixing the lines L1 and L2 by the function of the segmenting section 53 (see FIG. 4).

In the present embodiment, the range 11 to be imaged is segment into the two body parts, the chest and abdomen, by positioning the lines L1 and L2 at an upper end of the chest and an upper end of the abdomen, respectively.

Therefore, in FIG. 8, a region 11e surrounded by the line L1, sides 11b and 11d delineating the range 11 to be imaged, and the line L2 represents the chest. Moreover, a region 11f surrounded by the line L2, and sides 11b, 11c, and 11d delineating the range 11 to be imaged represents the abdomen. The length of the region 11e in the z-direction is z2, and the length of the region 11f in the z-direction is z3.

Figure 9:
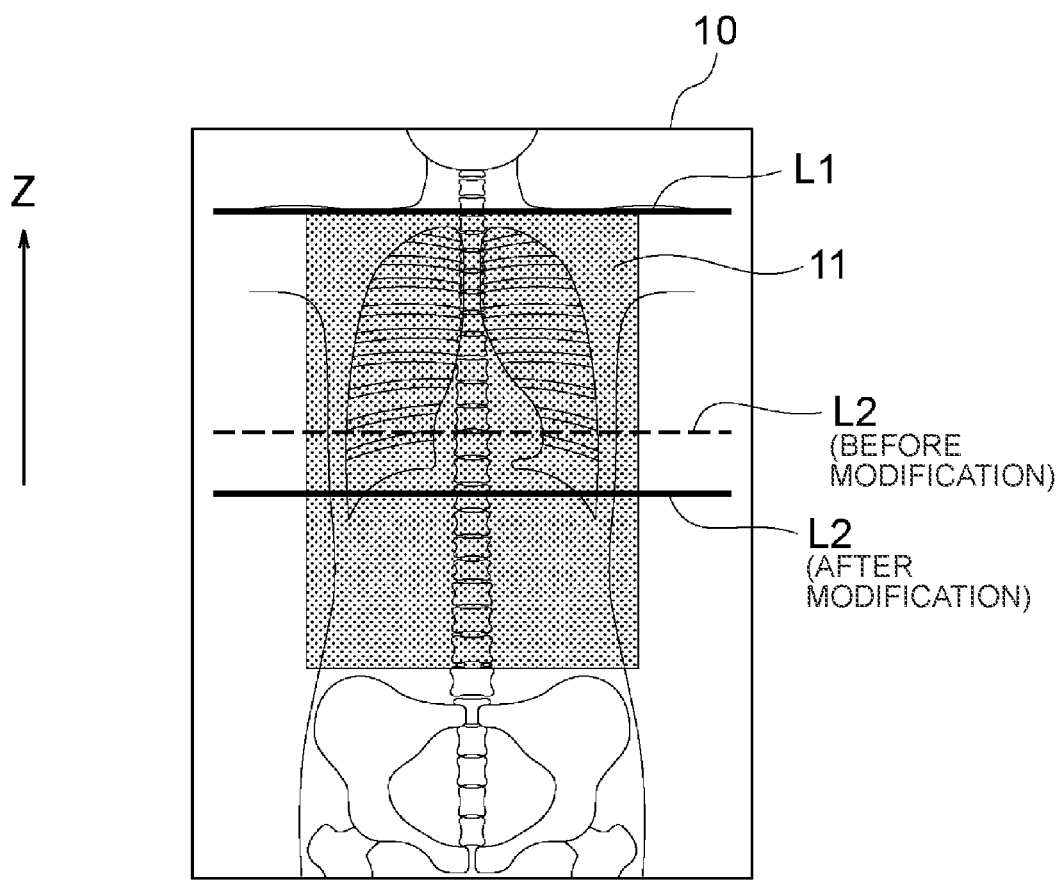
FIG. 9 is a diagram showing an example of modification of the position of line L2.

In the case that the radiologic technologist 8 desires to modify the position of the line L1 or L2 segmenting the range 11 to be imaged, the mouse, etc. may be used to manually modify the position of the line L1 or L2 (see FIG. 9).

FIG. 9 is a diagram showing an example of modification of the position of the line L2.

The line L2 before modification is indicated by a dashed line, while the line L2 after modification is indicated by a solid line.

In the case that the radiologic technologist 8 desires to adjust the position of the line L2 displayed over the scout image 10, (s)he uses the input device 61 to perform an operation for adjusting the position of the line L2. The radiologic technologist 8 may move the line L2 to a desired position by performing an operation of, for example, moving the cursor onto the line L2 and dragging the mouse. The display device 62 displays the modified line L2 over the scout image 10. Therefore, in the case that the initially fixed position of the line L2 (dashed line) is not suitable for segmenting the range 11 to be imaged into the chest and abdomen, the radiologic technologist 8 can easily modify the position of the line L2 to one suitable for segmenting the range 11 to be imaged into the chest and abdomen.

After fixing the lines L1 and L2, the flow goes to Step ST42.

At Step ST42 is identified to which ones of body parts a human body has a body part represented by the region 11e and a body part represented by the region 11f correspond.

Now an example of a method of the identification will be described hereinbelow.

The radiologic technologist 8 first uses the input device 61 to perform an operation for displaying over the scout image 10 a candidate body part(s) represented by the region 11e. The operation may involve, for example, an operation by the radiologic technologist 8 moving the cursor onto the line L1 and performing a mouse-click. The input device 61 inputs an operational signal corresponding to the operation by the radiologic technologist 8. In response to the operational signal input from the input device 61, the processor in the processing device 64 instructs the display device 62 to display the candidate body part(s) represented by the region 11e. In response to the instruction, the display device 62 loads a candidate list representing the candidate body parts stored in the storage device 63, and displays the loaded candidate list over the scout image 10 (see FIG. 10).

Figure 10:
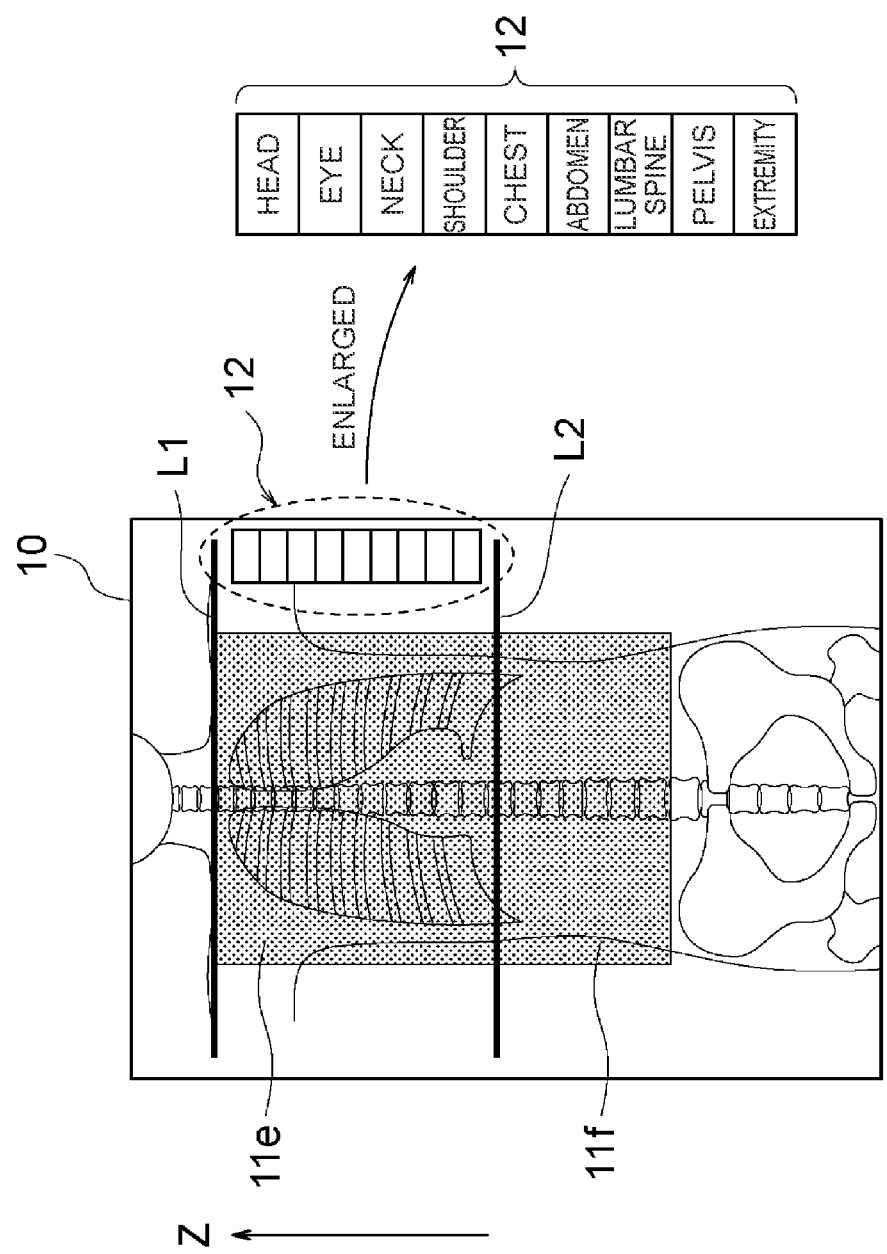
FIG. 10 is a diagram showing a candidate list displayed in the scout image 10.

FIG. 10 is a diagram showing the candidate list displayed in the scout image 10.

The candidate list includes a plurality of candidates 12. The plurality of candidates 12 may be displayed in the form of, for example, a pull-down menu. In FIG. 10, body parts included in a human body are classified into nine body parts ("Head," "Eye," "Neck," "Shoulder," "Chest," "Abdomen," "Lumber Spine," "Pelvis," and "Extremity"), which are displayed as the plurality of candidates 12. However, the plurality of candidates 12 are not limited to the nine body parts shown in FIG. 10. The human body may be divided into more than the nine body parts described above to obtain ten or more body parts as the plurality of candidates 12. On the contrary, the human body may be divided into less than the nine body part to obtain eight or less body parts as the plurality of candidates 12.

Figure 11:
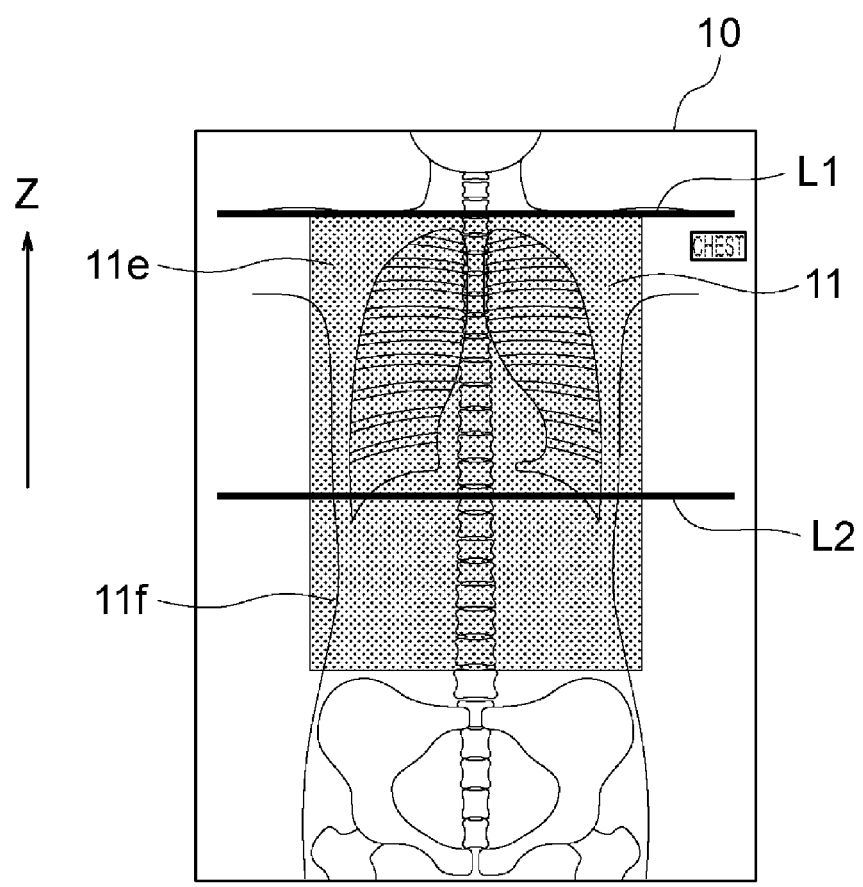
FIG. 11 is a diagram showing the scout image 10 after a radiology technologist 8 has selected the chest.

To identify which one of the plurality of candidates 12 the body part of the region 11e corresponds to, the radiologic technologist 8 selects a body part that corresponds to the body part of the region 11e from among the plurality of candidates 12. To make this selection, the radiologic technologist 8 uses the input device 61 to perform an operation for selecting "Chest" from among the plurality of candidates 12. The operation may involve, for example, an operation by the radiologic technologist 8 moving the cursor to a portion of the plurality of candidates 12 in which "Chest" is displayed, and performing a mouse-click. The input device 61 inputs an operational signal corresponding to the operation by the radiologic technologist 8. In response to the operational signal input from the input device 61, the processor in the processing device 64 selects "Chest" from among the plurality of candidates 12. The processor in the processing device 64 also instructs the display device 62 to display only "Chest" from among the plurality of candidates 12. The display device 62 can thus display "Chest" in the vicinity of the line L1, as shown in FIG. 11. The radiologic technologist 8 can recognize that "Chest" has been selected as the body part of the region 11e by observing the image in FIG. 11 displayed on the display device 62. Body-part information representing the fact that the region 11e is the chest is stored in the storage device 63. The processor in the processing device 64 may execute the processing of selecting "Chest" from among the plurality of candidates 12 by the function of the identifying section 54 (see FIG. 4).

Next, the radiologic technologist 8 specifies which body part the region 11f represents.

The body part of the region 11f may be specified by a similar method to that specifying the body part of the region 11e.

Figure 12:
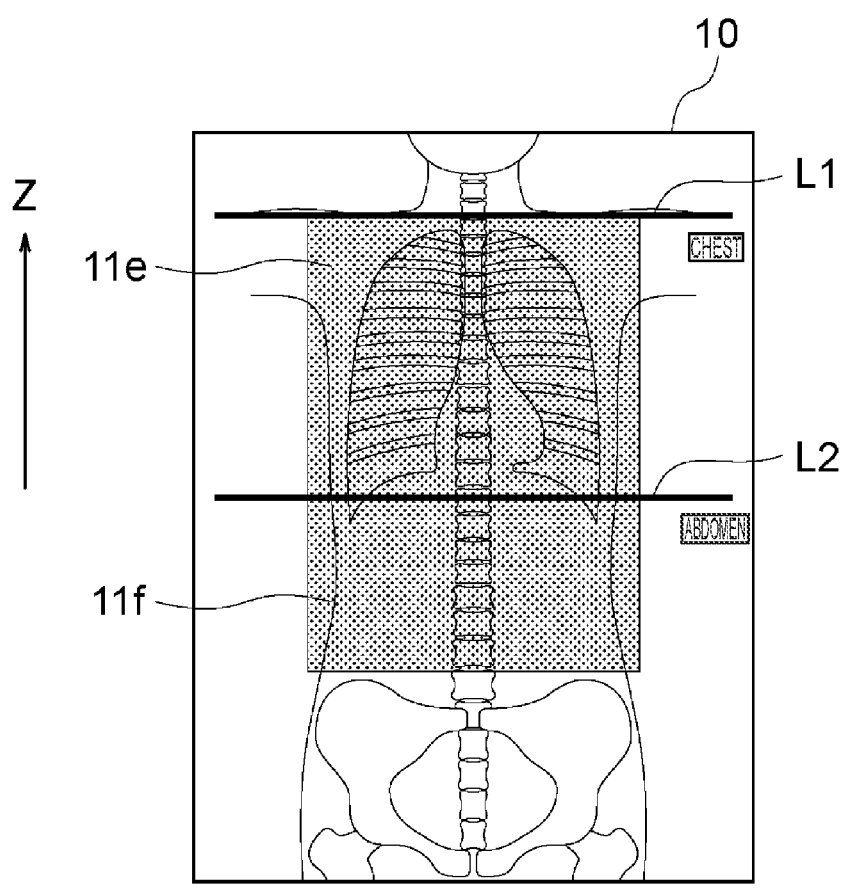
FIG. 12 is a diagram showing the scout image 10 after the radiology technologist 8 has selected the abdomen.

The radiologic technologist 8 displays the plurality of candidates 12 on the display device 62. Then, to specify which one of the plurality of candidates 12 the body part of the region 11f corresponds to, the radiologic technologist 8 selects a body part that corresponds to the body part of the region 11f from among the plurality of candidates 12. Since the body part of the region 11f is the abdomen, the radiologic technologist 8 selects the abdomen from among the plurality of candidates 12. By selecting the abdomen, "Abdomen" is displayed in the vicinity of the line L2, as shown in FIG. 12. The region 11f is thus identified as the abdomen. Body-part information representing the fact that the region 11f is the abdomen is then stored in the storage device 63.

In this way, the body parts of the regions 11e and 11f are identified. After identifying the body parts, the flow goes to Step ST5.

At Step ST5, a main scan for acquiring a CT image of the range 11 to be imaged is performed. After performing the main scan, the flow goes to Step ST6.

At Step ST6, the processor in the processing device 64 creates a dose report. It is assumed here that a scan range and a dose index are determined as fields required in the dose report. Now the scan range and dose index will be briefly described hereinbelow.
(On the Scan Range)

In the present embodiment, the processor in the processing device 64 calculates a scan range for each body part. In the main scan, body parts for which the scan ranges should be calculated are three body parts: a body part in the whole range 11 to be imaged, and two body parts that the radiologic technologist 8 has specified (the chest and abdomen). It is assumed here that a scan range is defined by the length of each body part in the z-direction. Therefore, the processor in the processing device 64 calculates a length of the body part in the whole range 11 to be imaged in the z-direction, and a length of the chest in the z-direction, and a length of the abdomen in the z-direction. The length of the body part in the whole range 11 to be imaged in the z-direction may be calculated based on the length z1 of the range 11 to be imaged in the z-direction that the radiologic technologist 8 has specified (see FIG. 7). The lengths of the chest and abdomen in the z-direction may be calculated based on the lengths z2 and z3 of the regions 11e and 11f in the z-direction, respectively (see FIG. 8). The processor in the processing device 64 may execute the processing of calculating a scan range for each body part by the function of the calculating section 55 (see FIG. 4). While the scan range is defined by the length of each body part in the z-direction here, the scan range may be defined by both the length of each body part in the z-direction and a length thereof in the x-direction.
(On the Dose Index)

In the present embodiment, the processor in the processing device 64 calculates a dose index for the body part in the whole range 11 to be imaged, and dose indices for the two body parts (the chest and abdomen) that the radiologic technologist 8 has specified. While the dose index may include, for example, CTDIvol (volume CTDI), and DLP (Dose-Length Product), dose indices other than CTDIvol and DLP (for example, EI) may be calculated. These dose indices can be calculated by a known method. The processor in the processing device 64 may execute the processing of calculating a dose index for each body part by the function of the calculating section 55 (see FIG. 4).

After calculating the scan ranges and dose indices, the processor in the processing device 64 creates a dose report including the scan ranges and dose indices. The processor in the processing device 64 may execute the processing of creating a report by the function of the report creating section 56 (see FIG. 4). After creating the report, the flow goes to Step ST7.

At Step ST7, the DICOM image and dose report, etc. are sent from the X-ray CT apparatus (modality M1) to the PACS 101 (see FIG. 1). The PACS 101 saves therein the image and dose report.

The flow thus ends.

As described above, in the present embodiment, the dose report is saved in the PACS 101. Therefore, the radiologic technologist 8 can load the dose report from the PACS 101 for display on the display device 62 of the X-ray CT apparatus 1, as needed (see FIG. 13).

FIG. 13 is a diagram showing an example of a displayed dose report.

In the dose report 13 is contained dose information regarding a main scan. Since the dose in a scout scan is very small, numeric values of the fields in the dose report 13 regarding the scout scan are omitted in FIG. 13.

FIG. 13 shows a case in which two axial scans and two Smart View scans have been executed as main scans. On the right side of these scans are shown numeric values of the scan ranges and two dose indices (CTDIvol and DLP), which are included in the fields of the dose report 13. (Although the numeric values of the fields are shown as "xxx" in FIG. 13, the numeric values calculated at Step ST6 are actually shown.)

Therefore, the radiologic technologist 8 can confirm the numeric values of the fields in the dose report 13 for the main scan by viewing the dose report 13. The radiologic technologist 8 can also confirm the numeric values of the fields for the two body parts (chest and abdomen) that the radiologic technologist 8 has specified at Step ST42 for every scan (see FIG. 14).

FIG. 14 is a diagram showing an example of the dose report 13 representing numeric values of the fields for the chest and those for the abdomen.

For example, in the case that the radiologic technologist 8 desires to confirm the numeric values of the fields for the chest and abdomen regarding a first axial scan executed in the main scan, (s)he uses the input device 61 to perform an operation for loading detailed information for the first axial scan. The input device 61 inputs an operational signal according to the operation by the radiologic technologist 8. In response to the operational signal input from the input device 61, the processor in the processing device 64 instructs the display device 62 to display the detailed information for the first axial scan. In response to the instruction, the display device 62 displays the detailed information for the first axial scan in the dose report 13, as shown in FIG. 14. In FIG. 14, the indications "CH" and "AB" are shown below the indication "Axial" representing the first axial scan. "CH" is an abbreviation of "Chest," representing the chest. "AB" is an abbreviation of "Abdomen," representing the abdomen. Therefore, the radiologic technologist 8 can confirm the numeric value of the dose index for the whole range 11 to be imaged, and in addition, those for the chest and abdomen on a body part-by-body part basis, and thus, the exposure dose for the patient 40 can be more particularly managed.

Figure 15:
FIG. 15 is a diagram showing an example of an abbreviation table.

It should be noted that the processor in the processing device 64 may produce an abbreviation table representing the relationships between abbreviations and body parts included in the dose report 13, and may include the abbreviation table into data to be sent to the PACS 101 (see FIG. 15).

FIG. 15 is a diagram showing an example of the abbreviation table.

In the abbreviation table 14 are shown abbreviations "HD," "ER," "NK," "SH," "CH," "AB," "LS," "PV," and "LE." "HD," "ER," "NK," "SH," "CH," "AB," "LS," "PV," and "LE" represent a head, an eye, a neck, a shoulder, a chest, an abdomen, a lumber spine, a pelvis, and an extremity, respectively.

The radiologic technologist 8 can confirm which body part of the patient 40 the abbreviations for the body parts shown in the dose report 13 represent by viewing the abbreviation table 14.

It should be noted that the present invention is not limited to the embodiment described above, and several additions, modifications, etc. may be applied.

For example, in the present embodiment, the lines L1 and L2 are used to distinguish the range 11 to be imaged as a plurality of body parts whose dose indices should be managed. However, the range 11 to be imaged may be segmented into the plurality of body parts without using the lines L1 and L2. For example, in place of the lines L1 and L2, there may be provided closed borders individually surrounding the plurality of body parts whose dose indices should be managed, and regions surrounded by the closed borders may be specified as the body parts whose dose indices should be managed. The closed borders in any shape may be used as such borders, and rectangular or circular closed borders may be used, for example.

Moreover, in the present embodiment, the radiologic technologist 8 specifies the range to be imaged at Step ST3. However, which body part of the patient 40 is to be imaged is information known beforehand prior to starting an examination on the patient 40. Accordingly, it is possible for the processor in the processing device 64 to automatically define the range to be imaged, rather than the radiologic technologist 8 specifying the range to be imaged. A method of automatic definition of a range to be imaged may be performed according to, for example, the procedure including (s1)-(s3) below:

(s1) The processor in the processing device 64 identifies a body part of the patient 40 to be imaged in the current examination. Generally, data managed in RIS, HIS, or the like includes data for identifying which body part of the patient 40 the body part to be imaged is. Therefore, the processor in the processing device 64 can identify a body part of the patient 40 to be imaged from the data managed in RIS or HIS. That is, the processor in the processing device 64 can know that the chest and abdomen are the body parts to be imaged from the data managed in RIS or HIS.

(s2) Next, the processor in the processing device 64 detects the body parts to be imaged identified at (s1) from among body parts rendered in the scout image 10. For a method of detection, for example, a known segmentation method, etc. involving segmenting individual organs rendered in an image may be used. The processor in the processing device 64 can detect a current body part to be imaged by performing segmentation on body parts rendered in the scout image 10 and analyzing the segmented body parts. It should be noted that an AI technique may be used to detect the current body part to be imaged.

(s3) Finally, the processor in the processing device 64 locates a region occupied by the plurality of detected body parts to be imaged (for example, the chest and abdomen) from within a human body region rendered in a CT image, such as the scout image 10, etc., and defines a range surrounding the located region as a range to be imaged.

According to the procedure including (s1)-(s3), the radiologic technologist 8 does not have to manually specify a range to be imaged, and therefore, an operational stress on the radiologic technologist 8 can be reduced.

Furthermore, in the present embodiment, the radiologic technologist 8 manually specifies the lines L1 and L2. However, the processor in the processing device 64 may detect body parts to be imaged from a CT image, such as the scout image 10, etc., and automatically define the lines L1 and L2 based on position information for the detected body parts to be imaged.

In addition, in the present embodiment, the radiologic technologist 8 selects body parts corresponding to the regions 11e and 11f from among the plurality of candidates 12. However, it is possible for the processor in the processing device 64 to identify which body part of the patient 40 the body part to be imaged is from the data managed in RIS, HIS, or the like, and thus, the processor in the processing device 64 may automatically identify body parts corresponding to the regions 11e and 11f.

Moreover, the present embodiment addresses a case in which the chest and abdomen of the patient 40 are included in the range to be imaged. However, the range to be imaged is not limited to the range including the chest and abdomen, and a range including body part(s) other than the chest and abdomen may be defined as the range to be imaged.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

The invention claimed is:

1. A medical apparatus comprising:
   image producing unit (51) for producing a scout image (10) of at least part of a patient (40);
   defining unit (52) for defining a range (11) to be imaged in said scout image (10);
   segmenting unit (53) for segmenting said range (11) to be imaged into a plurality of body parts;
   identifying unit (54) for identifying which one of body parts (12) included in a human body each of said plurality of body parts corresponds to; and
   calculating unit (55) for calculating a dose index for each of said plurality of body parts.

2. The medical apparatus as recited in claim 1, wherein: said segmenting unit (53) defines a line for segmenting said range (11) to be imaged into the plurality of body parts.

3. The medical apparatus as recited in claim 1, wherein: said identifying unit (54) selects a body part that corresponds to each body part included in said range (11) to be imaged from a list representing the body parts (12) included in a human body.

4. The medical apparatus as recited in claim 1, comprising: report creating unit (56) for creating a dose report (13) including said dose indices.

5. The medical apparatus as recited in claim 4, wherein:
   in said dose report (13) is shown by an abbreviation (14) a body part that corresponds to each of said plurality of body parts, and
   said report creating unit (56) creates abbreviation information representing a relationship between said abbreviation and the body part of said patient (40).

6. The medical apparatus as recited in claim 1, wherein: said dose indices include CTDIvol (volume CTDI), and DLP (Dose-Length Product).

7. The medical apparatus as recited in claim 1, comprising: a display device (62) for displaying said range (11) to be imaged segmented into said plurality of body parts.

8. The medical apparatus as recited in claim 1, comprising: an input device (61) for inputting an operational signal corresponding to a user's operation.

9. The medical apparatus as recited in claim 8, wherein: in response to the operational signal input from said input device (61) corresponding to said user's operation, said defining unit (52) defines said range (11) to be imaged in said scout image (10).

10. The medical apparatus as recited in claim 8, wherein: in response to the operational signal input from said input device (61) corresponding to said user's operation, said segmenting unit (53) segments said range (11) to be imaged into the plurality of body parts.

11. The medical apparatus as recited in claim 8, wherein: in response to the operational signal input from said input device (61) corresponding to said user's operation, said identifying unit (54) identifies which one of the body parts (12) included in said human body each of said plurality of body parts corresponds to.

12. A non-transitory, computer-readable recording medium provided in a medical apparatus for acquiring an image (10) of a patient (40), in which medium are stored one or more processor-executable instructions causing, when executed by a processor, execution of the acts comprising:
   producing a scout image (10) of at least part of a patient (40);
   defining a range (11) to be imaged in said scout image (10);
   segmenting said range (11) to be imaged into a plurality of body parts;
   identifying which one of body parts (12) included in a human body each of said plurality of body parts corresponds to; and
   calculating a dose index for each of said plurality of body parts.

* * * * *